(12) United States Patent
Tesconi et al.

(10) Patent No.: US 7,767,678 B2
(45) Date of Patent: Aug. 3, 2010

(54) CRYSTALLINE FORMS OF 4-[(2,4-DICHLORO-5-METHOXYPHENYL) AMINO]-6-METHOXY-7-[3-(4-METHYL-1-PIPERAZINYL)PROPOXY]-3-QUINOLINE CARBONITRILE AND METHODS OF PREPARING THE SAME

(75) Inventors: Marc Sadler Tesconi, Monroe, NY (US); Gregg Feigelson, Chester, NY (US); Henry Strong, Somerset, NJ (US); Hong Wen, Westfield, NJ (US)

(73) Assignee: Wyeth LLC, Madison, NJ (US)

( * ) Notice: Subject to any disclaimer, the term of this patent is extended or adjusted under 35 U.S.C. 154(b) by 147 days.

(21) Appl. No.: 11/478,216

(22) Filed: Jun. 29, 2006

(65) Prior Publication Data

US 2007/0015767 A1   Jan. 18, 2007

Related U.S. Application Data

(60) Provisional application No. 60/696,381, filed on Jul. 1, 2005.

(51) Int. Cl.
*A61K 31/497* (2006.01)
*C07D 241/04* (2006.01)
*C07D 295/00* (2006.01)

(52) U.S. Cl. .................... 514/252.12; 544/358
(58) Field of Classification Search ........... None
See application file for complete search history.

(56) References Cited

U.S. PATENT DOCUMENTS

| | | | |
|---|---|---|---|
| 6,002,008 A | 12/1999 | Wissner et al. | 546/160 |
| 6,432,979 B1 | 8/2002 | Frost et al. | 359/819 |
| 6,617,333 B2 | 9/2003 | Rabindram et al. | 514/291 |
| 2004/0229880 A1* | 11/2004 | Boschelli et al. | 514/253.06 |
| 2007/0010527 A1* | 1/2007 | Boschelli | 514/253.06 |

FOREIGN PATENT DOCUMENTS

| WO | WO 03/093241 | | 11/2003 |
|---|---|---|---|
| WO | WO 2004/075898 | * | 9/2004 |
| WO | WO 2005/019201 | | 3/2005 |
| WO | WO 2005/047259 | | 5/2005 |
| WO | WO2005/065074 | * | 7/2005 |
| WO | WO 2007001831 | * | 1/2007 |

OTHER PUBLICATIONS

Boschelli et al. Journal of Organic Chemistry, 2004, 47, 1599-1601, available online Feb. 27, 2004.*
Sakai et al. Tetrahedron: Asymmetry, 2004, 15, 3495-3500.*
Golas et al. Cancer Research, 2003, 63, 375-81.*
Boschelli et al., J. Med Chem., 44, 3965 (2001).

* cited by examiner

*Primary Examiner*—James O Wilson
*Assistant Examiner*—Noble Jarrell
(74) *Attorney, Agent, or Firm*—David Rubin; Stephen D. Prodnuk (57) ABSTRACT

This invention is directed to a crystalline 4-[(2,4-dichloro-5-methoxyphenyl)amino]-6-methoxy-7-[3-(4-methyl-1-piperazinyl)propoxy]-3-quinolinecarbonitrile monohydrate having an x-ray diffraction pattern wherein 2θ angles (°) of significant peaks are at about: 9.19, 11.48, 14.32, 19.16, 19.45, 20.46, 21.29, 22.33, 23.96, 24.95, 25.29, 25.84, 26.55, 27.61, and 29.51, and a transition temperature of about 109° C. to about 115° C.

21 Claims, 11 Drawing Sheets

CRYSTALLINE FORMS OF 4-[(2,4-DICHLORO-5-METHOXYPHENYL) AMINO]-6-METHOXY-7-[3-(4-METHYL-1-PIPERAZINYL)PROPOXY]-3-QUINOLINE CARBONITRILE AND METHODS OF PREPARING THE SAME

This invention claims the benefit of U.S. Provisional Application No. 60/696,381, filed Jul. 1, 2005.

BACKGROUND OF THE INVENTION

1. Field of the Invention

This invention is directed to crystalline forms of 4-[(2,4-dichloro-5-methoxyphenyl)amino]-6-methoxy-7-[3-(4-methyl-1-piperazinyl)propoxy]-3-quinolinecarbonitrile, methods of preparing these forms and pharmaceutical compositions containing them. These compounds are useful in treating cancers, particularly pancreatic and prostate cancer.

2. Related Background Art

3-Cyanoquinoline derivatives have been shown to have anti-tumor activity that may make them useful as chemoagents in treating various cancers, including pancreatic cancer, melanoma, lymphatic cancer, parotid tumors, Barrett's esophagus, esophageal carcinomas, head and neck tumors, ovarian cancer, breast cancer, epidermoid tumors, cancers of the major organs, such as kidney, bladder, larynx, stomach, and lung, colonic polyps and colorectal cancer and prostate cancer.

In the following U.S. patents, 3-cyanoquinoline derivatives are disclosed and shown to possess anti-tumor activity: U.S. Pat. Nos. 6,002,008; 6,432,979; and 6,617,333.

There continues to be a need for forms of 4-[(2,4-dichloro-5-methoxyphenyl)amino]-6-methoxy-7-[3-(4-methyl-1-piperazinyl)propoxy]-3-quinolinecarbonitrile that are more stable, but still possess a high degree of solubility.

BRIEF SUMMARY OF THE INVENTION

Figure 1:
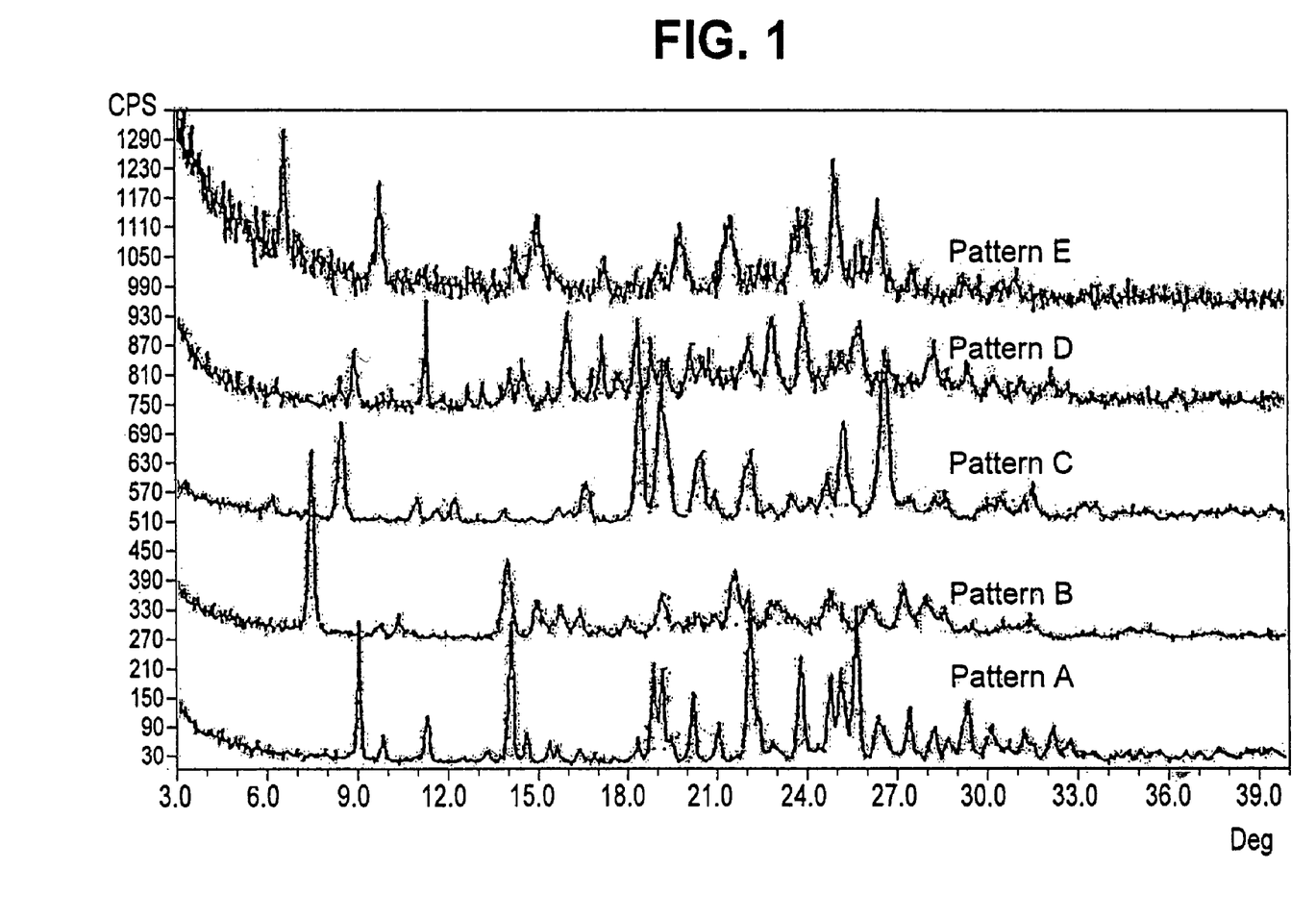
FIG. 1. The XRD scans of five different polymorphs of 4-[(2,4-dichloro-5-methoxyphenyl)amino]-6-methoxy-7-[3-(4-methyl-1-piperazinyl)propoxy]-3-quinolinecarbonitrile.
Figure 11:
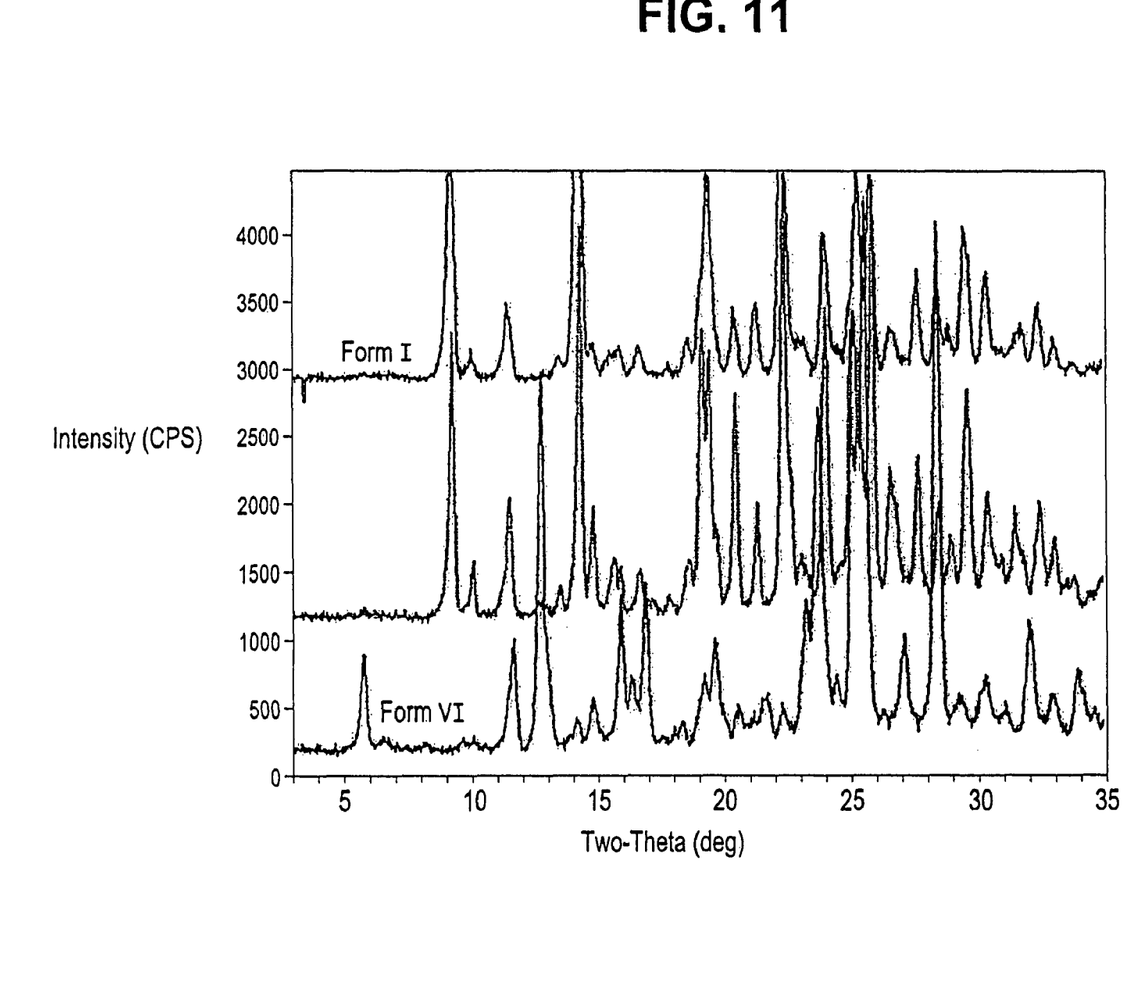
FIG. 11. The XRD scans of Form VI (bottom), Form I (top), as a standard, and the form resulting from exposing Form VI to hot water.

This invention is directed to isolated polymorphs of crystalline 4-[(2,4-dichloro-5-methoxyphenyl)amino]-6-methoxy-7-[3-(4-methyl-1-piperazinyl)propoxy]-3-quinolinecarbonitrile including Form I, Form II, Form III, Form IV, Form V and Form VI having x-ray diffraction patterns as shown in FIG. 1 and FIG. 11. A particular preferred polymorph is a monohydrate (Form I) having an x-ray diffraction pattern wherein at least one or more, and most preferably all, of the 2θ angles (°) of significant peaks are at about: 9.19, 11.48, 14.32, 19.16, 19.45, 20.46, 21.29, 22.33, 23.96, 24.95, 25.29, 25.84, 26.55, 27.61, and 29.51.

Another aspect of this invention is a crystalline 4-[(2,4-dichloro-5-methoxyphenyl)amino]-6-methoxy-7-[3-(4-methyl-1-piperazinyl)propoxy]-3-quinolinecarbonitrile monohydrate (Form I) having a transition temperature to a liquid of about 109° C. to about 115° C.

The invention is also directed to pharmaceutical compositions containing a therapeutically effective amount of crystalline 4-[(2,4-dichloro-5-methoxyphenyl)amino]-6-methoxy-7-[3-(4-methyl-1-piperazinyl)propoxy]-3-quinolinecarbonitrile, which has an x-ray diffraction pattern substantially as shown in FIGS. 1 and 11 selected from the group consisting of Patterns A, B, C, D, E and F, wherein more than 50% by weight of the crystalline 4-[(2,4-dichloro-5-methoxyphenyl)amino]-6-methoxy-7-[3-(4-methyl-1-piperazinyl)propoxy]-3-quinolinecarbonitrile present is one of the selected forms.

This invention is also directed to methods of preparing crystalline forms of 4-[(2,4-dichloro-5-methoxyphenyl)amino]-6-methoxy-7-[3-(4-methyl-1-piperazinyl)propoxy]-3-quinolinecarbonitrile, including the monohydrate, alcoholates, and mixtures of both. One method of preparing 4-[(2,4-dichloro-5-methoxyphenyl)amino]-6-methoxy-7-[3-(4-methyl-1-piperazinyl)propoxy]-3-quinolinecarbonitrile monohydrate (Form I) comprises the step of treating anhydrous 4-[(2,4-dichloro-5-methoxyphenyl)amino]-6-methoxy-7-[3-(4-methyl-1-piperazinyl)propoxy]-3-quinolinecarbonitrile, known herein as Form V, with heated water. Another method of preparing 4-[(2,4-Dichloro-5-methoxyphenyl)amino]-6-methoxy-7-[3-(4-methyl-1-piperazinyl)propoxy]-3-quinolinecarbonitrile monohydrate (Form I) comprises the step of converting other polymorphs of 4-[(2,4-Dichloro-5-methoxyphenyl)amino]-6-methoxy-7-[3-(4-methyl-1-piperazinyl)propoxy]-3-quinolinecarbonitrile, which have a x-ray diffraction pattern substantially the same as one of Patterns B, C, D and F, as shown in FIGS. 1 and 11, by treatment with water. The water can be heated or at a temperature where no heat source or cold source is applied, in which case the water would be at room temperature.

DETAILED DESCRIPTION

The present invention is directed to isolated crystalline 4-[(2,4-dichloro-5-methoxyphenyl)amino]-6-methoxy-7-[3-(4-methyl-1-piperazinyl)propoxy]-3-quinolinecarbonitrile, which can exist in six different forms, an anhydrous form and four different hydrated or alcoholated forms. As used herein the term "isolated" means that more than 50% of the crystalline 4-[(2,4-dichloro-5-methoxyphenyl)amino]-6-methoxy-7-[3-(4-methyl-1-piperazinyl)propoxy]-3-quinolinecarbonitrile present is one of Forms I, II, III, IV, V and VI and more preferably at least 70% to 90% of the crystalline 4-[(2,4-dichloro-5-methoxyphenyl)amino]-6-methoxy-7-[3-(4-methyl-1-piperazinyl)propoxy]-3-quinolinecarbonitrile present is in one of Forms I, II, III, IV, V and VI.

Figure 10:
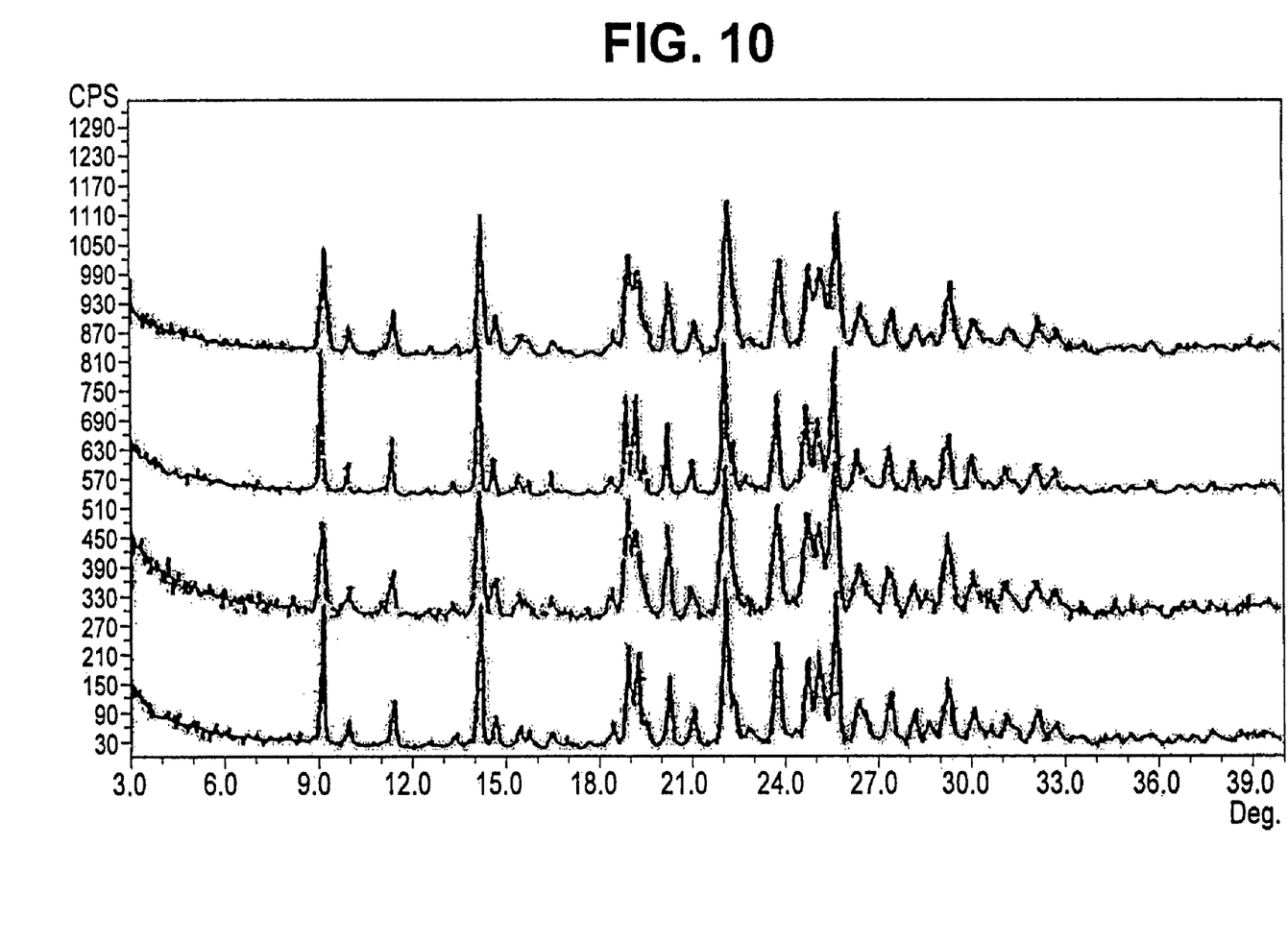
FIG. 10. The XRD scan of five batches of Form I.

Form I is a monohydrate and is more stable than the other polymorph forms. It gives substantially Pattern A when scanned by XRD as shown in FIGS. 1 and 10. Form I generally does not lose water when exposed to 0% relative humidity for 10 days, or when heated to 90° C. for over 100 hours. Form I is not hygroscopic, as it generally only gains about 0.52% weight when subjected to about 90% relative humidity, as shown by the dynamic vapor sorption plot in FIG. 2. Form I also possesses the highest transition temperature of all the hydrated forms.

Figure 5:
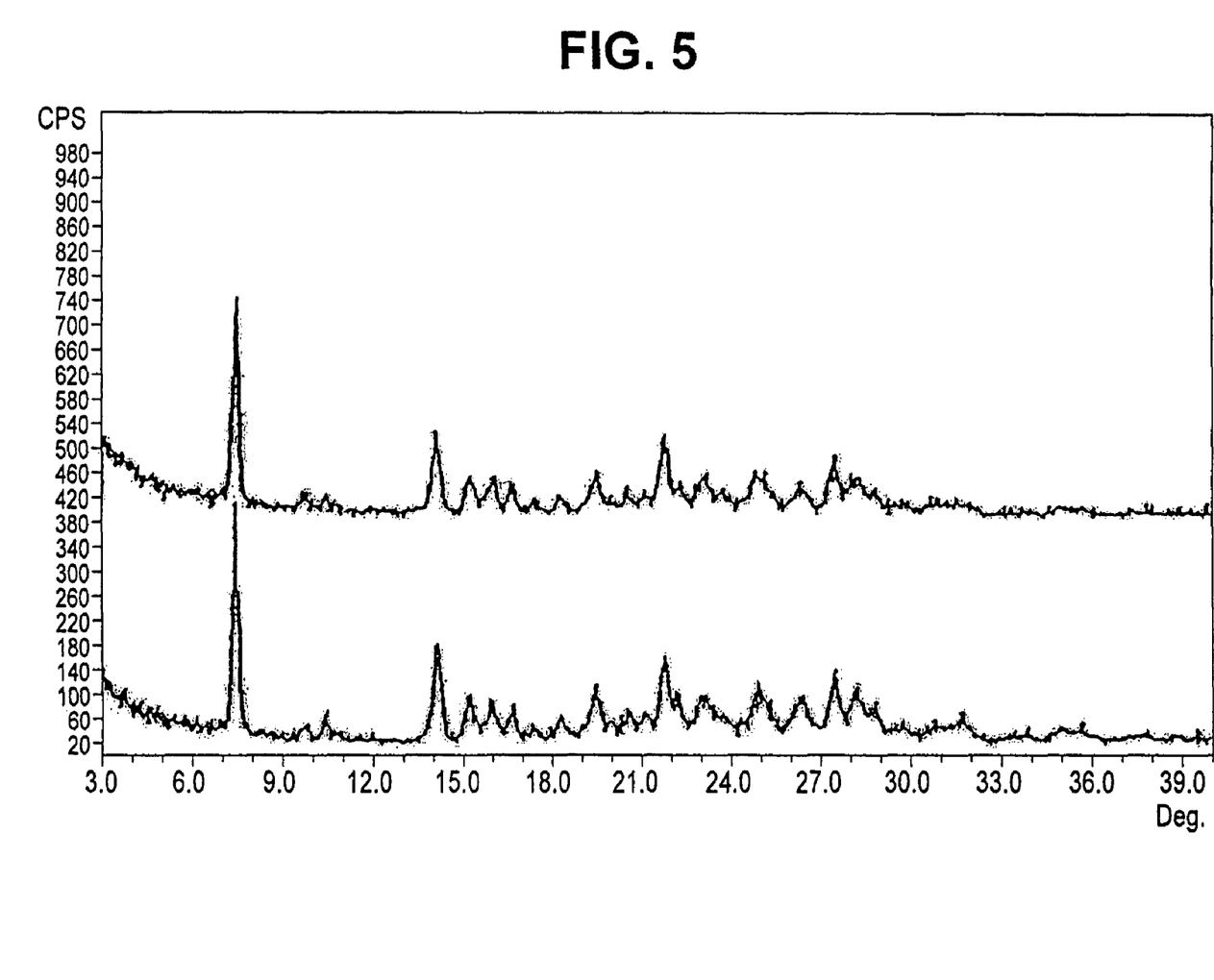
FIG. 5. The XRD scan of two batches of Form II.
Figure 6:
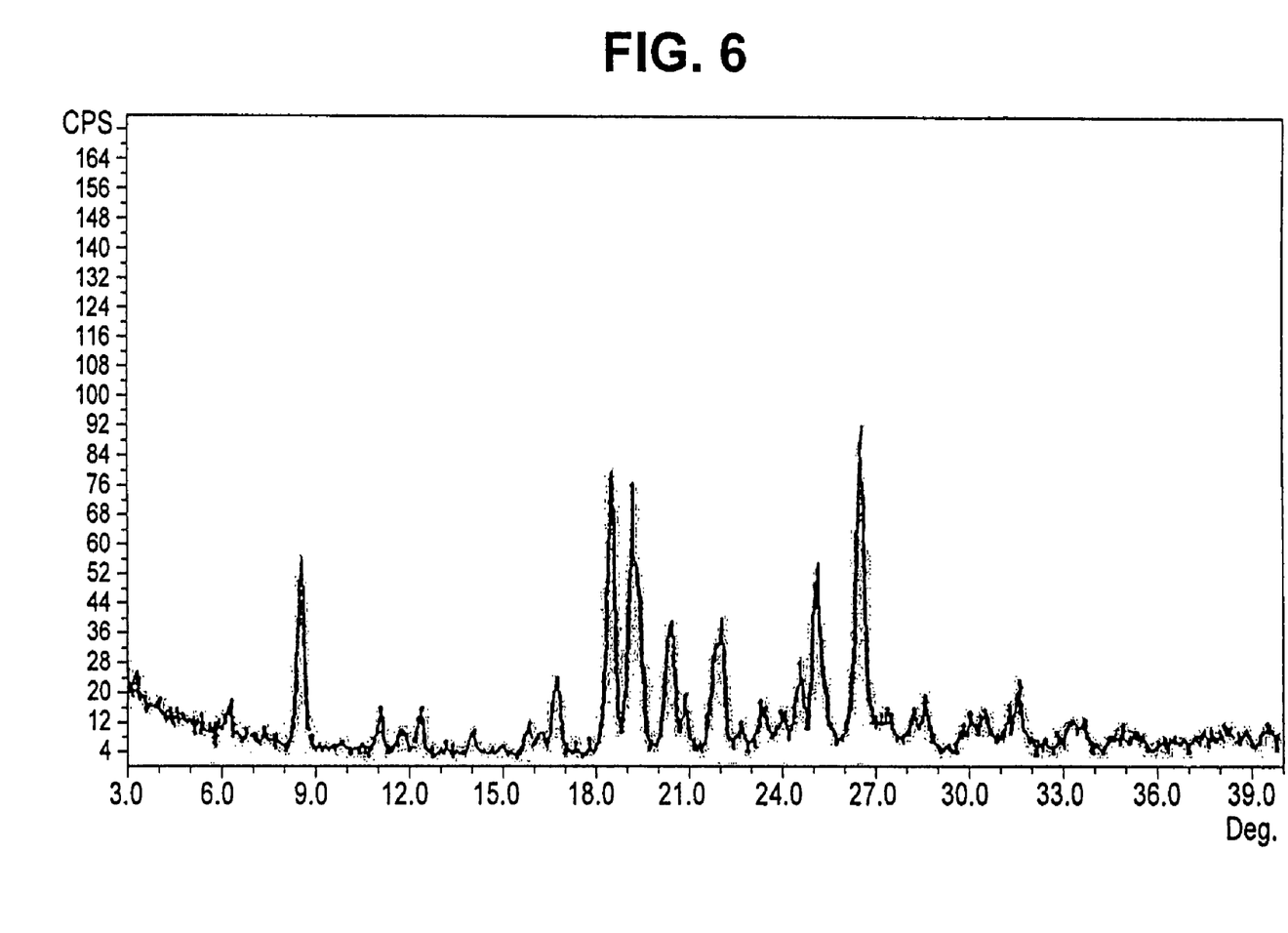
FIG. 6. The XRD scan of Form III.
Figure 7:
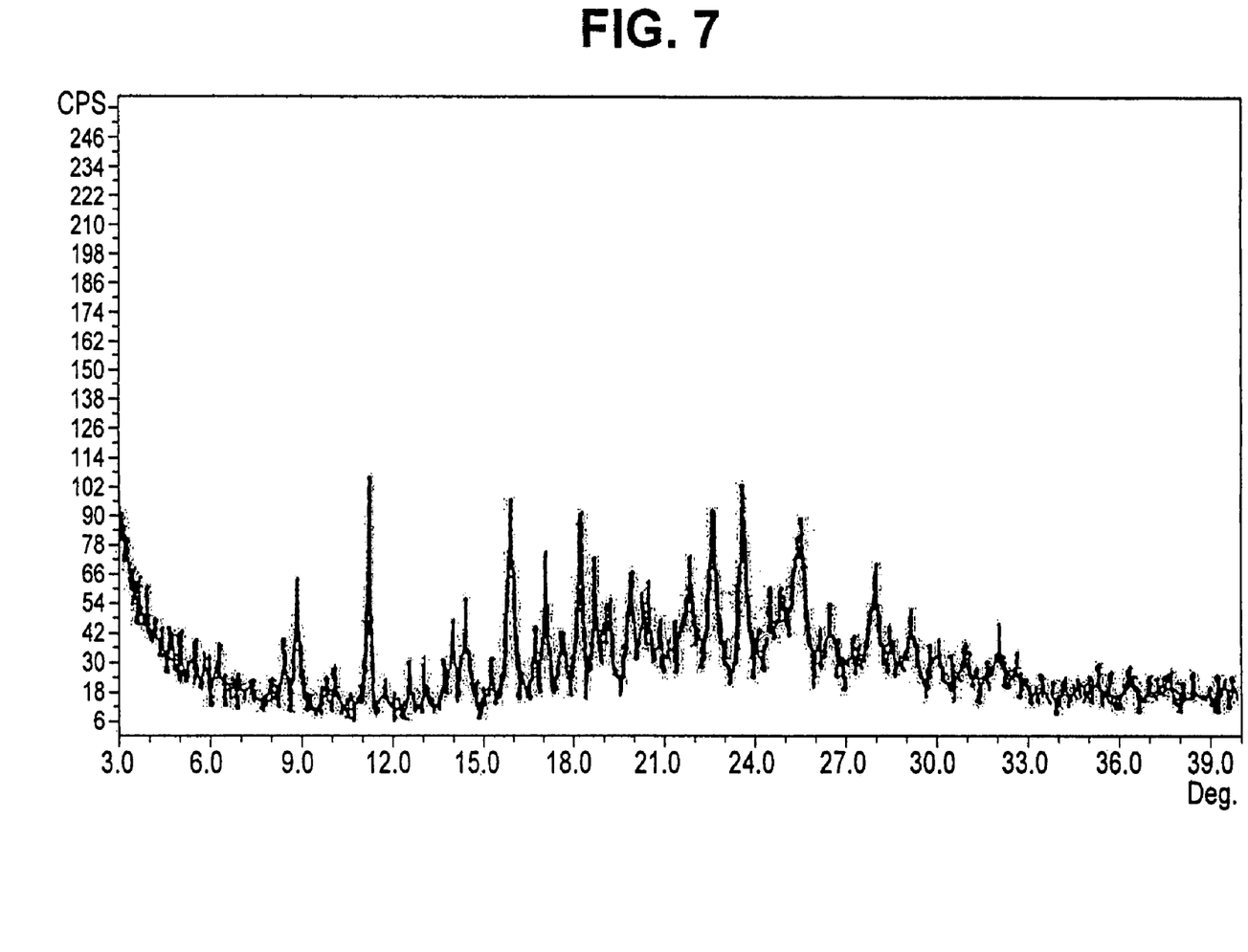
FIG. 7. The XRD scan of Form IV.

Form II is also a monohydrated form as determined by Karl Fisher analysis and when scanned by XRD gives substantially Pattern B shown in FIGS. 1 and 5. Form III is a monoisopropyl alcoholate as determined by GLC and NMR. Form IV is likely a hydrated polymorph, though its structure is unclear. When scanned by XRD, Forms III and IV, give substantially Patterns C and D, as shown in FIGS. 6 and 7, respectively. Form VI is a methanolate form and gives substantially XRD Pattern F, as shown in FIG. 11.

Forms II, III, IV and Form VI can all be transformed into Form I by treatment with water, e.g. by heating in water. The water may be at room temperature. The water may be heated to at least about 90° C., and as high as at least about 95° C.

Figure 8:
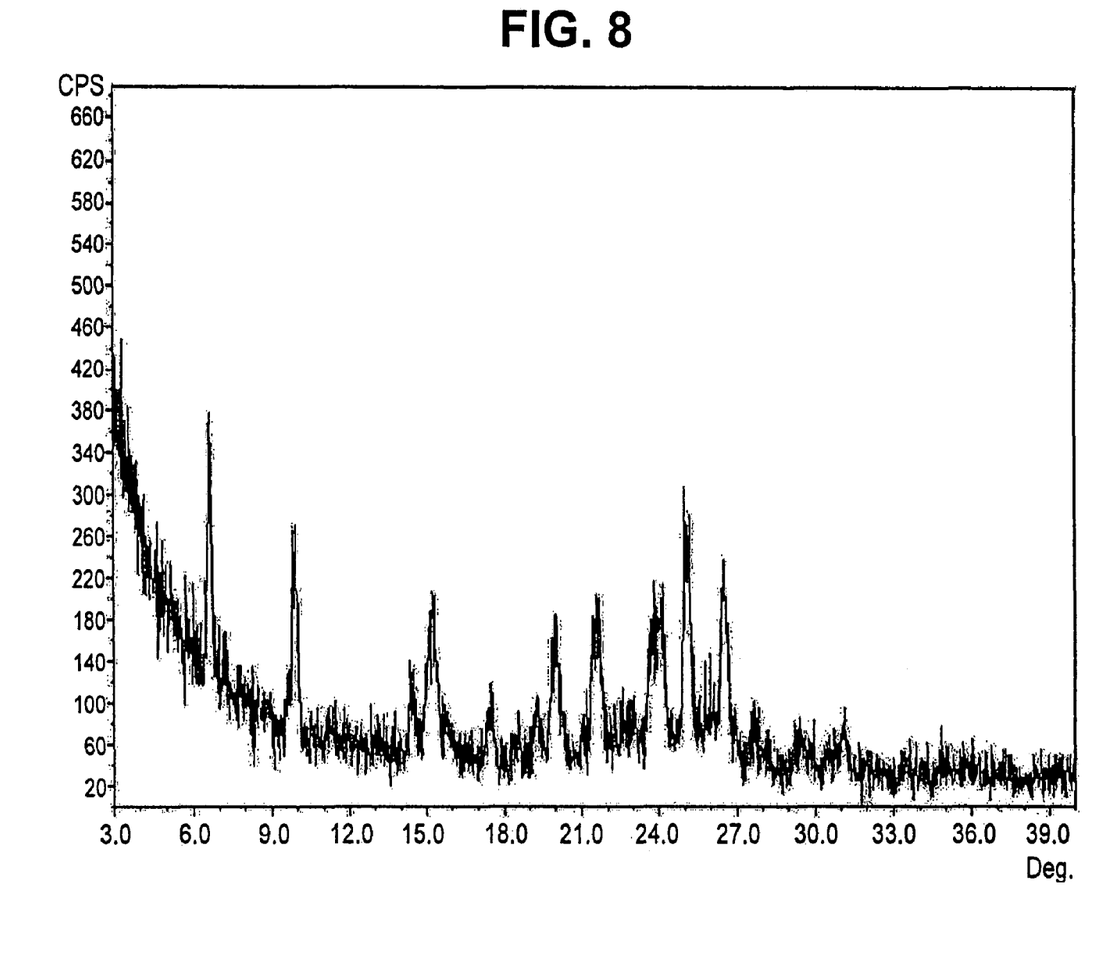
FIG. 8. The XRD scan of Form V.

Form V is the anhydrous form, producing substantially Pattern E in FIGS. 1 and 8 when scanned by XRD, and has the highest transition temperature of all the polymorphic forms, i.e., about 148° C. It is also readily converted to Form I by treatment with heated water. The water is heated to at least about 90° C., and more preferably is heated to at least about 95° C. In addition, Form V can be converted into a hydrated Form II by treatment with water at room temperature over a period of 2 months, as shown by differential scanning calorimetry and thermogravimetric analysis in FIG. 3. This hydrated form is different from either Form I or V, as shown by the XRD scan in FIG. 4. For this reason Form I is viewed as the more stable form, even though Form V has the higher transition temperature.

Shown in Table 1 are 2θ angles from the x-ray diffraction patterns of Forms II, III, IV and V. It should be understood that at least one of these peaks must be present in a given form, and preferably at least a majority of the listed peaks will be present for a given form. In a most preferred embodiment all the peaks are present for a given form, although one skilled in the art will recognize that whether all the peaks are observed for a given form may be highly dependent on the concentration level of the form.

TABLE 1

XRD 2θ Angles for Patterns B (Form II),
C (Form III), D (Form IV) and E (Form V).

| Form II 2θ | Form III 2θ | Form IV 2θ | Form V 2θ |
|---|---|---|---|
| 7.62 | 6.28 | 8.58 | 6.70 |
| 9.89 | 8.64 | 9.04 | 10.00 |
| 10.49 | 11.17 | 11.5 | 14.45 |
| 14.19 | 11.81 | 12.94 | 15.27 |
| 15.24 | 12.45 | 13.42 | 17.49 |
| 16.08 | 14.11 | 14.33 | 19.94 |
| 16.76 | 15.92 | 14.73 | 20.06 |
| 18.46 | 16.88 | 16.27 | 21.65 |
| 21.79 | 18.75 | 17.46 | 24.14 |
| 23.16 | 19.44 | 17.83 | 25.24 |
| 24.88 | 20.70 | 18.65 | 26.55 |
| 26.36 | 21.17 | 19.46 | |
| 27.40 | 22.36 | 20.38 | |
| 28.28 | 24.88 | 20.72 | |
| 28.76 | 25.42 | 22.29 | |
| | 26.81 | 23.02 | |
| | | 24.05 | |
| | | 26.00 | |

Form I is also more stable, and therefore more desirable, because it can withstand exposure to various environments for a prolonged period of time with out degradation. For example, Form I has remained substantially pure and physically unchanged after being exposed to 510 foot-candles (~5490 lux) light for two weeks, 75% humidity at 40° C. for 3 months, and 90° C. for 2 weeks, as determined by XRD and HPLC.

Form I has the highest transition temperature of all the hydrated forms. Typically Form I upon heating dehydrates between 95° C. and 100° C. and then transitions to a liquid in the range of 109° C. to 115° C., but the most likely transition temperature, when substantially pure, is 112° C. The other hydrated forms usually transition to a liquid between 76° C. to 90° C. Table 2 shows the transition temperatures of the various forms.

TABLE 2

List of different batches in different crystal forms.

| Pattern (XRD) | Crystallization | Solid to Liquid Transition temperatures and Comments |
|---|---|---|
| A | refluxed in 95° C. water | Transitions at 112° C., monohydrate |
| | Acetone/water (3/1) | Transitions at 112° C., monohydrate |
| | IPA/H20 (1/1) | Transitions 109-115° C., monohydrate, low crystallinity |
| | Acetone/water (2/1) | Transitions at 112° C., monohydrate |
| | Acetone/water | Transitions at 94° C., monohydrate |
| B | IPA/H20 (2/1) | Transitions at 90° C.,) Converts to "I" in 95° C. water |
| C | IPA/H2O (2/1) | Transitions at 82° C., 11.5% weight loss by TGA indicates that it is a monoisopropyl alcoholate Converts to "I" in 95° C. water |
| D | Acetone/water, (7/2) | Transitions at 76° C. Converts to "I" in 90° C. water |
| | Acetone/water | Transitions at 80° C. |
| E | Acetone/water | Transitions at 145° C. Converts to "I" in 95° C. water |
| F | Methanol | Converts to "I" in 95° C. water |

The XRD patterns of Forms I, II, III, IV, V or VI can be determined by using techniques and equipment known to those skilled in the art of analytical chemistry and X-ray crystallography. The XRD patterns shown in FIGS. 1, 4, 5, 6, 7, 8 and 11 were produced using X-ray powder diffraction (Scintag Inc., Cupertino, Calif.), with voltage at 45 kV, current at 40.0 mA, power at 1.80 kW, a scan range (2θ) of 3° to 40°, scan step size of 0.02°, and a total scan time of 22'38".

The XRD patterns shown in FIGS. 1, 4, 5, 6, 7, 8, 10 and 11 were produced using powder samples. The XRD pattern for each form is unique to that form. Each pattern is comprised of a set of diffraction peaks, which can be expressed in 2 theta angles, d-spacing and/or relative peak intensities.

The 2 theta diffraction angles and the corresponding d-spacing values account for the positions of the peaks found in a XRD pattern. D-spacing values are calculated with observed 2 theta angles and copper Kα1 wavelength using the Bragg equation. Variations in these numbers can result from using different diffractometers and also from the method of sample preparation. However, more variation can be expected for the relative peak intensities. Therefore, identification of the various forms should be based upon the observed 2 theta angles and the d-spacings, and less importance should be given to the intensities.

Form I has at least one, preferably a majority and most preferably all, of the following characteristic 2 theta angles (°) peaks: 9.19, 9.98, 11.48, 14.32, 14.85, 15.64, 19.16, 19.45, 19.71, 20.46, 21.29, 22.33, 22.58, 23.96, 24.95, 25.29, 25.84, 26.55, 27.61, 28.42, 29.51, 30.32, 31.40, and 32.39.

One skilled in the art would understand that the XRD patterns of Forms I, II, III, IV, V and VI obtained as described herein could contain additional peaks.

The water content of the forms described herein was measured by the Karl Fisher method, which is well known to those skilled in the art, using a 756 KF Brinkmann Coulometer, with HYDRANAL-WATER Standard 1.00 used as the standard.

Figure 3A:
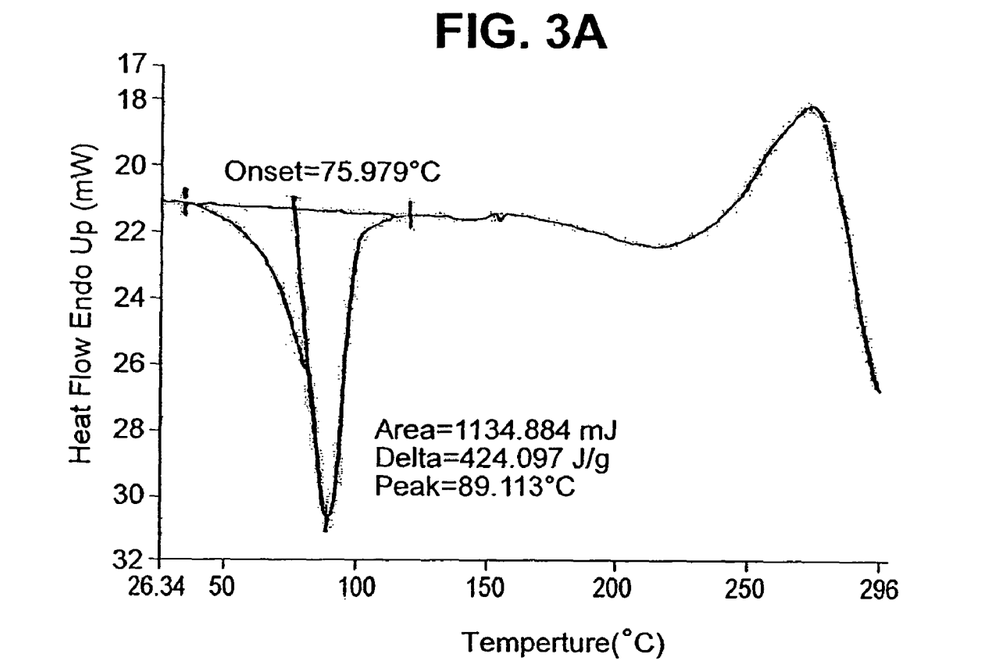
FIG. 3. A differential scanning calorimeter plot and a theromogravimetric analysis plot of Form V after suspension in water for two months and ten days at room temperature.
Figure 3B:
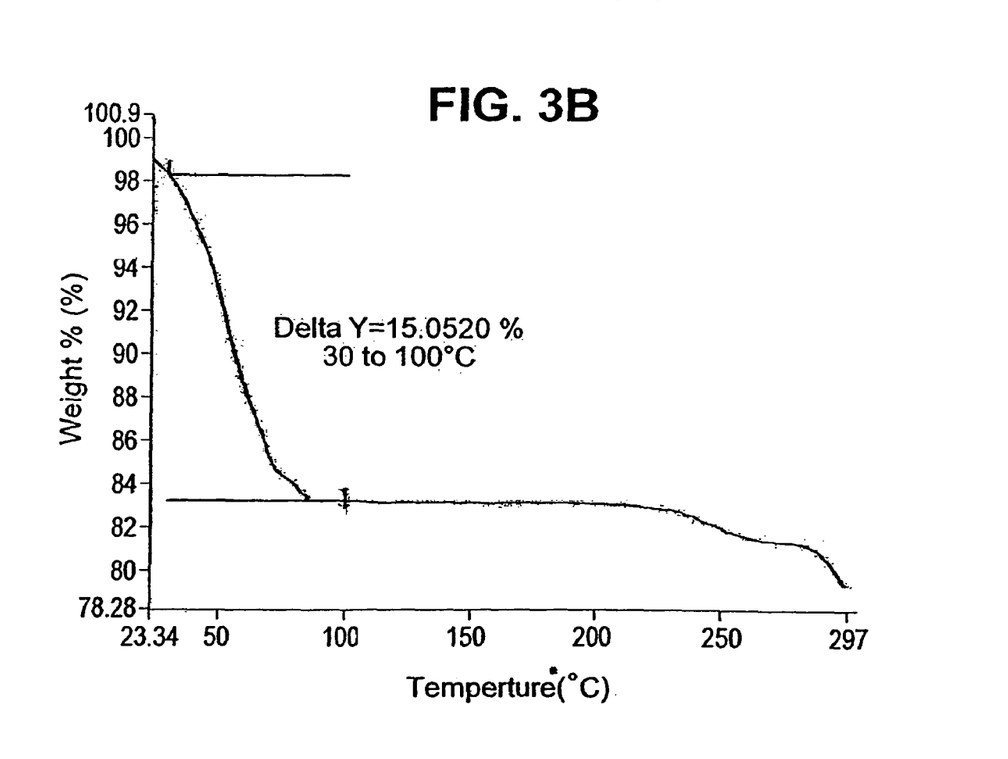
Figure 9A:
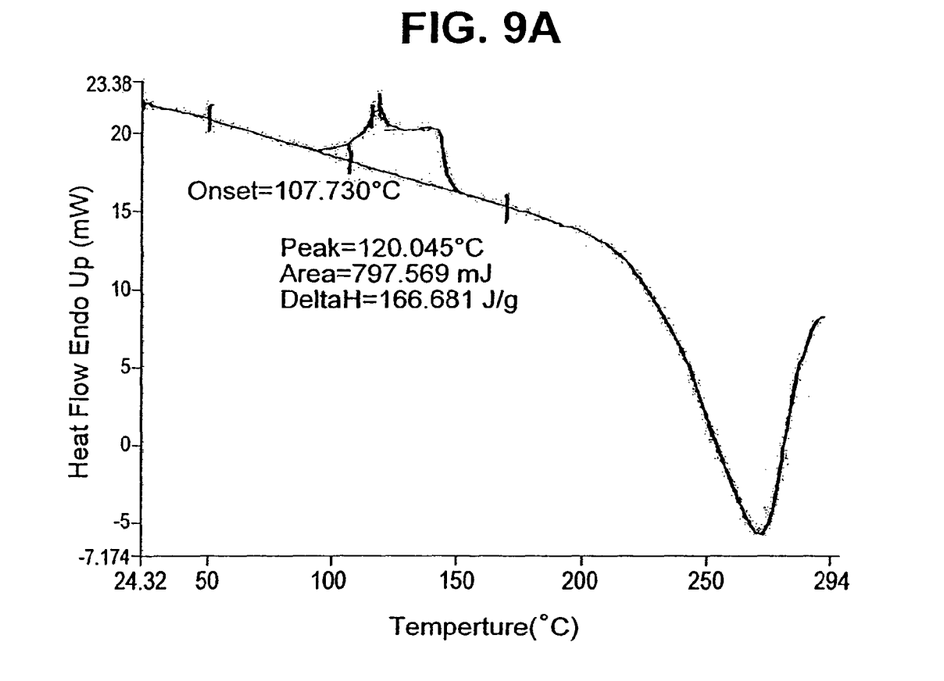
FIG. 9. A differential scanning calorimeter plot and a theromogravimetric analysis plot of Form I.
Figure 9B:
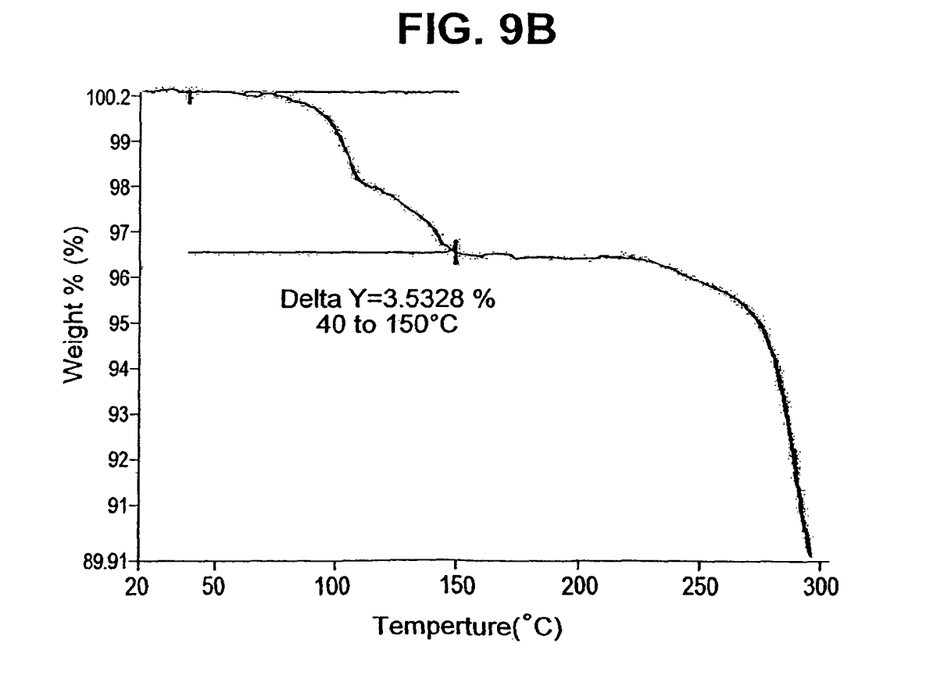

The water content of the hydrated forms described herein, including FIGS. 3 and 9, was measured using thermogravimetric analysis. A Perkin Elmer thermogravimetric analyzer was used for these analyses. The conditions were a 20 mL/minute nitrogen gas purge, a scan range of 25° C. to 300° C., and a scan rate of 10° C./minute.

Figure 2:
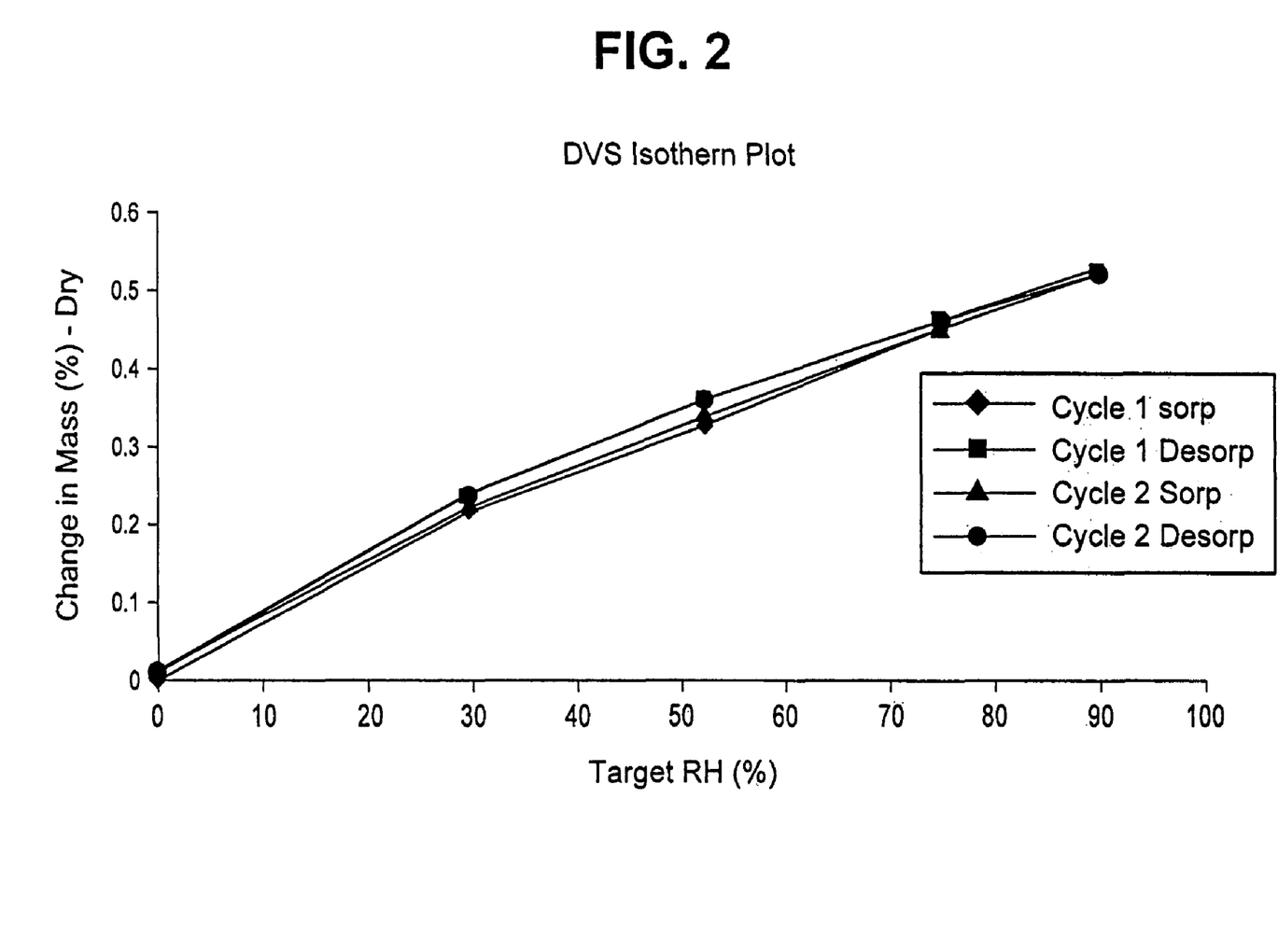
FIG. 2. A dynamic vapor sorption isotherm plot of Form I.

The hydroscopicity of the anhydrous Form V and the hydrated forms was determined using dyanamic vapor sorption, including the plot for Form I shown in FIG. 2. This was performed under the following conditions. RH was set at 0%, 30%, 52.5%, 75% and 90%, with the sample exposed for 3 hours at each RH for two full cycles.

Transition temperatures and heat flow for the various forms, including the plot shown in FIGS. 3 and 9, was determined using a Perkin Elmer differential scanning calorimeter. The conditions were a 20 mL/minute nitrogen gas purge, a scan range of 25° C. to 300° C., and a scan rate of 10° C./minute.

Pure, crystalline solids have a characteristic transition temperature, the temperature at which point the substance changes state, in the present case the solid transitions to a liquid. The transition between the solid and the liquid is so sharp for small samples of a pure substance that transition temperatures can be measured to 0.1° C. Because it is difficult to heat solids to temperatures above their transition temperatures, and because pure solids tend to transition over a very small temperature range, transition temperatures are often used to help identify compounds. Measurements of the transition temperature of a solid can also provide information about the purity of the substance. Pure, crystalline solids transition over a very narrow range of temperatures, whereas mixtures transition over a broad temperature range. Mixtures also tend to transition at temperatures below the transition temperatures of the pure solids.

The crystalline compounds of the present invention may be provided orally, by intralesional, intraperitoneal, intramuscular or intravenous injection; infusion; liposome-mediated delivery; topical, nasal, anal, vaginal, sublingual, urethereal, transdermal, intrathecal, ocular or otic delivery. In order to obtain consistency in providing the compound of this invention it is preferred that a compound of the invention is in the form of a unit dose. Suitable unit dose forms include tablets, capsules and powders in sachets or vials. Such unit dose forms may contain from 0.1 to 300 mg of a compound of the invention and preferably from 2 to 100 mg. Still further preferred unit dosage forms contain 50 to 150 mg of a compound of the present invention. The crystalline compounds of the present invention can be administered orally. Such compounds may be administered from 1 to 6 times a day, more usually from 1 to 4 times a day. The effective amount will be known to one of skill in the art; it will also be dependent upon the form of the compound. One of skill in the art could routinely perform empirical activity tests to determine the bioactivity of the compound in bioassays and thus determine what dosage to administer.

The crystalline compounds of the invention may be formulated with conventional excipients, such as a filler, a disintegrating agent, a binder, a lubricant, a flavoring agent, a color additive, or a carrier. The carrier may be for example a diluent, an aerosol, a topical carrier, an aqueous solution, a nonaqueous solution or a solid carrier. The carrier may be a polymer or a toothpaste. A carrier in this invention encompasses any of the standard pharmaceutically accepted carriers, such as phosphate buffered saline solution, acetate buffered saline solution, water, emulsions such as an oil/water emulsion or a triglyceride emulsion, various types of wetting agents, tablets, coated tablets and capsules.

When provided orally or topically, such compounds would be provided to a subject by delivery in different carriers. Typically, such carriers contain excipients such as starch, milk, sugar, certain types of clay, gelatin, stearic acid, talc, vegetable fats or oils, gums, or glycols. The specific carrier would need to be selected based upon the desired method of delivery, for example, phosphate buffered saline (PBS) could be used for intravenous or systemic delivery and vegetable fats, creams, salves, ointments or gels may be used for topical delivery.

The crystalline compounds of the present invention may be delivered together with suitable diluents, preservatives, solubilizers, emulsifiers, adjuvants and/or carriers useful in treatment or prevention of neoplasm. Such compositions are liquids or lyophilized or otherwise dried formulations and include diluents of various buffer content (for example, Tris-HCl, acetate, phosphate), pH and ionic strength, additives such as albumins or gelatin to prevent absorption to surfaces, detergents (for example, TWEEN 20, TWEEN 80, PLURONIC F68, bile acid salts), solubilizing agents (for example, glycerol, polyethylene glycerol), anti-oxidants (for example ascorbic acid, sodium metabisulfate), preservatives (for example, thimerosal, benzyl alcohol, parabens), bulking substances or tonicity modifiers (for example, lactose, mannitol), covalent attachment of polymers such as polyethylene glycol, complexation with metal ions, or incorporation of the compound into or onto particulate preparations of hydrogels or liposomes, micro-emulsions, micelles, unilamellar or multilamellar vesicles, erythrocyte ghosts, or spheroblasts. Such compositions will influence the physical state, solubility, stability, rate of in vivo release, and rate of in vivo clearance of the compound or composition. The choice of compositions will depend on the physical and chemical properties of the compound capable of treating or preventing a neoplasm.

The crystalline compounds of the present invention may be delivered locally via a capsule that allows a sustained release of the compound over a period of time. Controlled or sustained release compositions include formulation in lipophilic depots (for example, fatty acids, waxes, oils).

One embodiment of the composition of the present invention comprises a therapeutically effective amount of at least one of the crystalline forms of 4-[(2,4-dichloro-5-methoxy-7-[3-(4-methyl-1-piperazinyl)propoxy]-3-quinolinecarbonitrile, which has an x-ray diffraction pattern substantially as shown in FIGS. 1 and 11 selected from the group consisting of Patterns A, B, C, D, E and F, and a pharmaceutical acceptable carrier. In a preferred embodiment more than 50%, more preferably at least 80%, more preferably greater than 90% by weight of the crystalline form is Form I. A more specific embodiment is where this composition comprises either acetic acid or a detergent, or both. More preferably the composition will comprise acetic acid in a weight percentage range of about 0.01% to about 0.1% and the detergent in a weight percentage range of about 0.5% to about 5.0%. The most preferred embodiment of this composition is where it is comprised of about 2.0% by weight detergent and about 0.06% by weight acetic acid.

Another preferred embodiment of the composition of the present invention comprises a therapeutically effective amount of at least one of the crystalline forms of 4-[(2,4-dichloro-5-methoxy-7-[3-(4-methyl-1-piperazinyl)propoxy]-3-quinolinecarbonitrile, which has an x-ray diffraction pattern substantially as shown in FIGS. 1 and 11 selected from the group consisting of Patterns A, B, C, D, E and F, and a pharmaceutical acceptable carrier that is selected from a sugar or polyol or cellulose. In a preferred embodiment more than 50%, more preferably at least 80%, more preferably greater than 90% of the crystalline form is Form I, having a x-ray diffraction pattern substantially the same as Pattern A, as shown in FIG. 1. A more preferred embodiment is where the sugar or polyol could be mannitol, sorbitol, or xylitol, with mannitol being the most preferred. In a more specific embodiment the composition would contain both mannitol and cellulose, and more preferably the crystalline forms of 4-[(2,4-dichloro-5-methoxy-7-[3-(4-methyl-1-piperazinyl)propoxy]-3-quinolinecarbonitrile, the mannitol and the cellulose are individually present in amounts of about 20 to about 50 percent by weight. The most preferred embodiments of the composition of the present invention are shown in Table 3.

TABLE 3

| | Composition No. | |
|---|---|---|
| Contents (% w/w) of Compositions | | |
| Ingredients | 1 | 2 |
| Crystalline form of 4-[(2,4-dichloro-5-methoxy-7-[3-(4-methyl-1-piperazinyl)propoxy]-3-quinolinecarbonitrile | 26.32 | 41.67 |
| A surfactant, such as poloxamer | 3.00 | 3.00 |
| A disintegrant, such as crospovidone | 3.00 | 3.00 |
| Cellulose, micro crystalline | 25.00 | 25.00 |
| Mannitol | 42.18 | 26.83 |
| A lubricant or stabilizer, such as magnesium stearate | 0.25 | 0.25 |

4-[(2,4-dichloro-5-methoxyphenyl)amino]-6-methoxy-7-[3-(4-methyl-1-piperazinyl)propoxy]-3-quinolinecarbonitrile is a weak base with an intrinsic (neutral form) solubility of approximately 0.06 μg/mL at pH 8.0. It is partially ionized in de-ionized water where it dissolves to 1.8μg/mL with a resulting pH of 7.2. Solubility is enhanced about 100-fold to 0.1 to 0.4 mg/mL with the addition of about 2% Tween80, a detergent. Solubility is further enhanced to 3-4 mg/mL (~1000-fold) with the addition of about 0.06% acetic acid (in-situ acetate salt vehicle). The acetate formulation has the advantage of eliminating variability in solubility due to polymorphism (see Table 4 below).

4-[(2,4-dichloro-5-methoxyphenyl)amino]-6-methoxy-7-[3-(4-methyl-1-piperazinyl)propoxy]-3-quinolinecarbonitrile has poor water solubility and wettability. However, due to the success in solubilizing the compound in the in-situ acetate salt vehicle, micronization is not required for formulation. Furthermore, with the high solubility (>200 mg/mL) and better wettability in stomach acid, micronization is also not required for human formulation.

TABLE 4

Solubility Information for 4-[(2,4-dichloro-5-methoxyphenyl)amino]-6-methoxy-7-[3-(4-methyl-1-piperazinyl)propoxy]-3-quinolinecarbonitrile.

| | Batch Size (g) | | | | | |
|---|---|---|---|---|---|---|
| | 95 | 50 | 120 | 54 | 18.5 | 550 |
| Use | Rat/Dog MTD(1v) | Rat PK(PO) | Rat MTD (PO) | Dog PK(PO) | Genotoxicity | Dog MTD (PO) |
| Water content % (1¢) | 3.68 | 3.27 | 3.24 | 7.06 | 3.76 | 336. |
| Particle Size μm (Malvert) | N/D | 50% = 9.87 90% < 20.2 | 50% 10.2 90% < 30.0 | 50% 11.7 90% < 24.1 | 50% = 10.5 90% < 29.1 | 50% = 8.3 90% < 20.8 |
| Polymorphism (XRD) | Pattern A | Pattern A | Pattern D | Pattern D | N/D | Pattern A |
| Solubility (mg/mL2 | | | | | | |
| Water | 0.0018 (pH 7.2) | N/D* | N/D* | N/D* | N/D | N/D |
| 2% Tween 80/03% MC | 0.16 (pH 8.3) | 0.20 (pH 8.4) | 0.07 (pH 7.7) | 0.06 (pH 7.8) | N/D | 0.41 (pH 7.4) |
| 2% Tween 80/0.5% MC 0.06% acetic acid | 4.0 (pH 5.4) | N/D | 3.5 (pH 5.0) | 2.68 (pH 5.2) | N/D | 4.25 (pH 5.7) |

N/D = Not Determined.
*Milled batches contained a significant amount of fines, which could not be removed from solution by centrifugation. Filtration led to erroneously low measurements due to the adsorption of solubilized 4-[(2,4-dichloro-5-methoxyphenyl)amino]-6-methoxy-7-[3-(4-methyl-1-piperazinyl)propoxy]-3-quinolinecarbonitrile to the filter material.

The dose provided to a patient will vary depending upon what is being administered, the purpose of the administration, the manner of administration, and the like. A "therapeutically effective amount" is an amount sufficient to cure or ameliorate symptoms of the disease being treated, such as cancer.

The crystalline compounds of this invention may be delivered alone or in combination with other compounds.

4-[(2,4-dichloro-5-methoxyphenyl)amino]-6-methoxy-7-[3-(4-methyl-1-piperazinyl)propoxy]-3-quinolinecarbonitrile was prepared as described in Scheme 1. 7-(3-chloropropoxy)-4-[(2,4-dichloro-5-methoxyphenyl)amino]-6-methoxy-3-quinolinecarbonitrile, 1, was alkylated with N-methylpiperazine in the presence of sodium iodide either neat or in a solvent such as ethylene glycol dimethyl ether. This preparation has been reported in the literature, [Boschelli, D. H., et. al., J. Med. Chem., 44, 3965 (2001)].

Scheme 1

-continued

DETAILED DESCRIPTION OF THE DRAWINGS

FIG. 1. The XRD scans of five different polymorphs of 4-[(2,4-dichloro-5-methoxyphenyl)amino]-6-methoxy-7-[3-(4-methyl-1-piperazinyl)propoxy]-3-quinolinecarbonitrile. The crystalline monohydrate, Form I, is shown as Pattern A, while the crystalline anhydrous form, Form V, is shown as Pattern E. Patterns B, C and D are from three other polymorphs of 4-[(2,4-dichloro-5-methoxyphenyl)amino]-6-methoxy-7-[3-(4-methyl-1-piperazinyl)propoxy]-3-quinolinecarbonitrile, or mixture of polymorphs, which have not been fully characterized.

FIG. 2. This is a dynamic vapor sorption plot which shows that 4-[(2,4-dichloro-5-methoxyphenyl)amino]-6-methoxy-7-[3-(4-methyl-1-piperazinyl)propoxy]-3-quinolinecarbonitrile monohydrate, Form I, gained only 0.52% from 0% RH to 90% RH. Therefore, this form must be considered non-hydroscopic.

FIG. 3. This is a differential scanning calorimeter (DSC) plot and a theromogravimetric analysis (TGA) plot of Form V after suspension in water for two months and ten days at room temperature. The low transitioning temperature shown in the DSC and the rapid dehydration shown in the TGA indicates that after suspension in water for two months and ten days indicates that the anhydrate has hydrated to a metastable hydrate crystal form.

Figure 4:
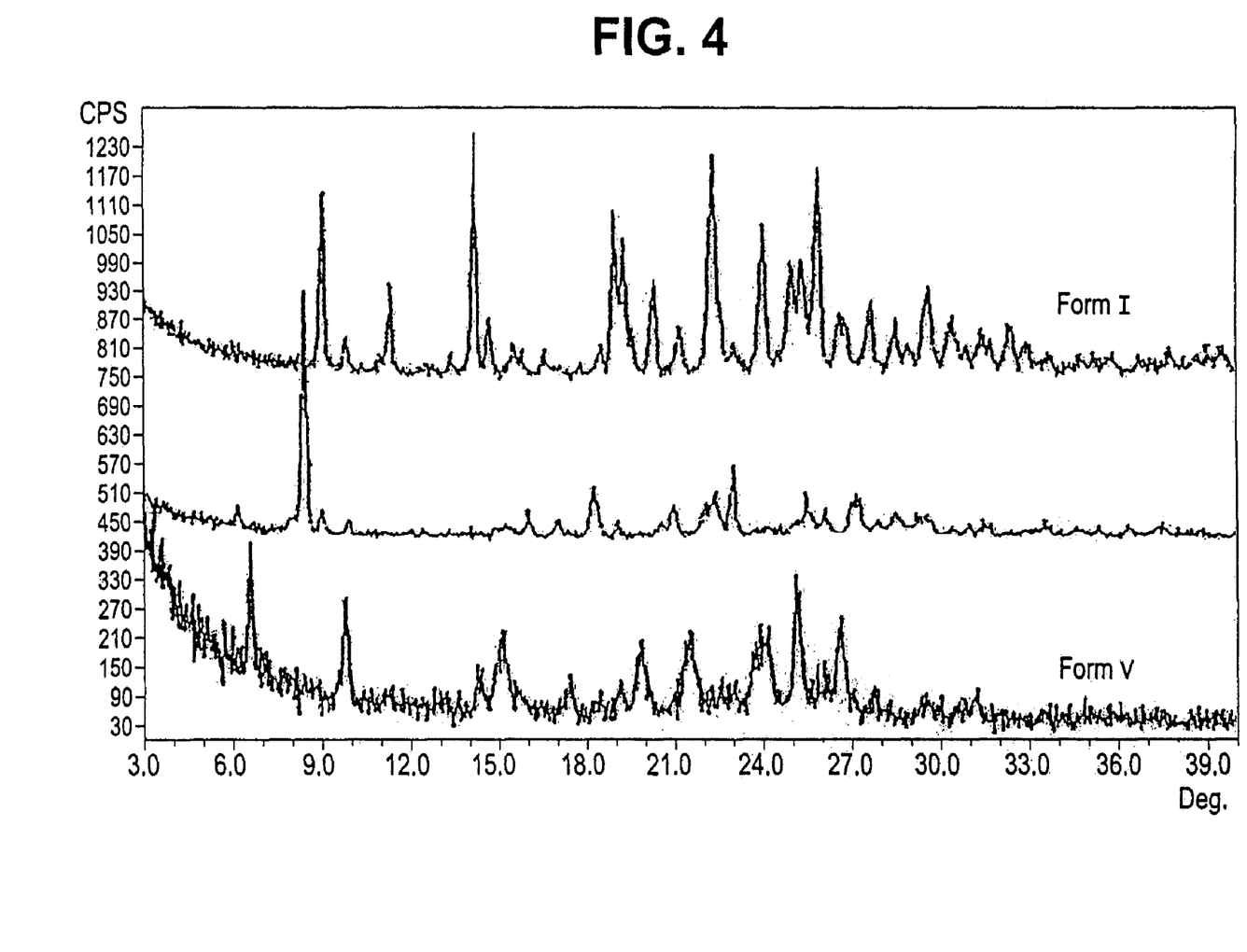
FIG. 4. The XRD scans of Form I, Form V and the metastable hydrate created after Form V is left suspended in water for two months and ten days at room temperature.

FIG. 4. XRD scans of Form I, Form V and Form V after it was suspended in water for two months and ten days at room temperature, which shows that the metastable hydrate which results from this exposure has a different structure than either Form I or Form V.

FIG. 5. An XRD scan of two different batches of Form II, which is a crystalline monohydrate of 4-[(2,4-dichloro-5-methoxyphenyl) amino]-6-methoxy-7-[3-(4-methyl-1-piperazinyl)propoxy]-3-quinoline carbonitrile.

FIG. 6. An XRD scan of crystalline 4-[(2,4-dichloro-5-methoxyphenyl) amino]-6-methoxy-7-[3-(4-methyl-1-piperazinyl)propoxy]-3-quinoline carbonitrile in Form III.

FIG. 7. An XRD scan of crystalline 4-[(2,4-dichloro-5-methoxyphenyl) amino]-6-methoxy-7-[3-(4-methyl-1-piperazinyl)propoxy]-3-quinoline carbonitrile in Form IV.

FIG. 8. An XRD scan of the anhydrous crystalline form of 4-[(2,4-dichloro-5-methoxyphenyl)amino]-6-methoxy-7-[3-(4-methyl-1-piperazyinyl)propoxy]-3-quinoline carbonitrile, Form V.

FIG. 9. This is a DSC plot and a TGA plot of Form I. The DSC plot shows that Form I has a transitioning range of about 108° C. to 120° C. The TGA plot evidences that Form I is a monohydrate since it shows that there is approximately a 3.5% loss of weight upon heating to 150° C.

FIG. 10. An XRD scan of five batches of crystalline 4-[(2,4-dichloro-5-methoxyphenyl)amino]-6-methoxy-7-[3-(4-methyl-1-piperazinyl)propoxy]-3-quinolinecarbonitrile monohydrate in Form I.

FIG. 11. XRD scans of Form VI (bottom), Form I (top), and the form resulting from heating Form VI in water (middle). Thus, it is shown that Form VI can be converted from into Form I by exposure to water, like Forms II, III, IV and V.

This invention will be more fully described in conjunction with the following specific example, which should not to be construed as limiting the scope of this invention.

EXAMPLE 1

Preparation of 4-[(2,4-dichloro-5-methoxyphenyl) amino]-6-methoxy-7-[3-(4-methyl-1-piperazinyl) propoxy]-3-quinolinecarbonitrile monohydrate, Form I, from Form V Non-crystalline 4-[(2,4-dichloro-5-methoxyphenyl) amino]-6-methoxy-7-[3-(4-methyl-1-piperazinyl)propoxy]-3-quinolinecarbonitrile was crystallized from a solution of 50:50 (v/v) acetone and water to give Form V. The resulting crystalline solid was recovered by filtration, and then suspended in water heated to about 80° C. for approximately 5 minutes. This mixture was then filtered to yield the titled compound and having a transitioning range of 109° C. to 115° C.

EXAMPLE 2

Preparation of 4-[(2,4-dichloro-5-methoxyphenyl) amino]-6-methoxy-7-[3-(4-methyl-1-piperazinyl) propoxy]-3-quinolinecarbonitrile monohydrate, Form I 4-[(2,4-Dichloro-5-methoxyphenyl)amino]-6-methoxy-7-[3-(4-methyl-1-piperazinyl)propoxy]-3-quinolinecarbonitrile (1.8 kg), isopropyl alcohol (12 L), and water (6 L) were added to a 50-L flask under nitrogen. The mixture was heated to 75° C. and filtered through a polypropylene cloth. The mixture was cooled to room temperature—crystallization began at about 37° C. The mixture was cooled further to 4° C. and then filtered. The cake was washed with 5 L of a 50/50 mixture of isopropyl alcohol/water (v/v). The resulting wet cake and 14 L of water were added to a 50-L flask. The mixture was heated to 95° C. and held for 5 hours. The hot mixture was filtered through a polypropylene cloth, filter cake washed with 2.5 L of water, and dried in a forced air oven at 40° C. to give 1.37 kg of 4-[(2,4-dichloro-5-methoxyphenyl) amino]-6-methoxy-7-[3-(4-methyl-1-piperazinyl)propoxy]-3-quinolinecarbonitrile Form I by XRD scans.

EXAMPLE 3

Preparation of 4-[(2,4-dichloro-5-methoxyphenyl) amino]-6-methoxy-7-[3-(4-methyl-1-piperazinyl) propoxy]-3-quinolinecarbonitrile, Form II 4-[(2,4-Dichloro-5-methoxyphenyl)amino]-6-methoxy-7-[3-(4-methyl-1-piperazinyl)propoxy]-3-quinolinecarbonitrile (5 g) and 50 mL of a mixture of 2/1 isopropyl alcohol/water (v/v) were added to a 125 mL flask, and heated to reflux. The mixture was cooled over night to room temperature and then to 5° C. After filtration, the cake was washed with 15 mL of a 2/1 mixture of isopropyl alcohol/water (v/v) and vacuum dried at 45° C. to give 3.92 g of 4-[(2,4-dichloro-5-methoxyphenyl)amino]-6-methoxy-7-[3-(4-methyl-1-piperazinyl) propoxy]-3-quinolinecarbonitrile, Form II by XRD scans.

EXAMPLE 4

Preparation of 4-[(2,4-dichloro-5-methoxyphenyl) amino]-6-methoxy-7-[3-(4-methyl-1-piperazinyl) propoxy]-3-quinolinecarbonitrile monoisopropyl alcoholate, Form III 4-[(2,4-Dichloro-5-methoxyphenyl)amino]-6-methoxy-7-[3-(4-methyl-1-piperazinyl)propoxy]-3-quinolinecarbonitrile (5 g) and 40 mL of a mixture of 2/1 isopropyl alcohol/water (v/v) were added to a 125 flask, and heated to reflux. The mixture was cooled over night to room temperature and filtered. The cake was washed with 15 mL of a 2/1 mixture of isopropyl alcohol/water (v/v) and vacuum dried at 45° C. to give 4.51 g of 4-[(2,4-dichloro-5-methoxyphenyl)amino]-6-methoxy-7-[3-(4-methyl-1-piperazinyl)propoxy]-3-quinolinecarbonitrile monoisopropyl alcoholate as determined by GLC and NMR and determined to be Form III by XRD scans.

EXAMPLE 5

Preparation of 4-[(2,4-dichloro-5-methoxyphenyl) amino]-6-methoxy-7-[3-(4-methyl-1-piperazinyl) propoxy]-3-quinolinecarbonitrile monoisopropyl alcoholate, Form III 4-[(2,4-Dichloro-5-methoxyphenyl)amino]-6-methoxy-7-[3-(4-methyl-1-piperazinyl)propoxy]-3-quinolinecarbonitrile (5 g) and 40 mL of a mixture of 2/1 isopropyl alcohol/water (v/v) were added to a 125 flask and heated to 70° C. The hot mixture was filtered; the filtrate was heated to 70° C. to redissolve the material. The mixture was cooled to room temperature. Crystallization began at about 45° C. After stirring overnight, the mixture was cooled to 5° C. The cake was washed with 15 mL of a 2/1 mixture of isopropyl alcohol/water (v/v) and then with 20 mL of water to give 6.58g of wet 4-[(2,4-dichloro-5-methoxyphenyl)amino]-6-methoxy-7-[3-(4-methyl-1-piperazinyl)propoxy]-3-quinolinecarbonitrile. A sample of the wet product (0.30 g) was vacuum dried at 40° C. to give 0.19 g of of 4-[(2,4-dichloro-5-methoxyphenyl) amino]-6-methoxy-7-[3-(4-methyl-1-piperazinyl)propoxy]-3-quinolinecarbonitrile monoisopropyl alcoholate as determined by GLC and NMR and determined to be Form III by XRD scans.

EXAMPLE 6

Preparation of 4-[(2,4-dichloro-5-methoxyphenyl) amino]-6-methoxy-7-[3-(4-methyl-1-piperazinyl) propoxy]-3-quinolinecarbonitrile, Form IV 4-[(2,4-Dichloro-5-methoxyphenyl)amino]-6-methoxy-7-[3-(4-methyl-1-piperazinyl)propoxy]-3-quinolinecarbonitrile (5 g) and 30 mL of acetone were added to a 100-mL flask and heated to reflux to give a solution. The hot mixture was filtered to clarify. The small amount of residue on filter paper was washed with 3 ml of acetone. Water (10 ml) was added to the hot filtrate. The mixture was cooled to 0-5° C. with an ice-water bath and filtered. The cake was washed with 15 ml of a 3/1 mixture of acetone/water (v/v) water and vacuum dried at 45° C. to give 3.48 g of 4-[(2,4-dichloro-5-methoxyphenyl)amino]-6-methoxy-7-[3-(4-methyl-1-piperazinyl) propoxy]-3-quinolinecarbonitrile, Form IV by XRD scans.

EXAMPLE 7

Preparation of 4-[(2,4-dichloro-5-methoxyphenyl) amino]-6-methoxy-7-[3-(4-methyl-1-piperazinyl) propoxy]-3-quinolinecarbonitrile, Form VI 4-[(2,4-Dichloro-5-methoxyphenyl)amino]-6-methoxy-7-[3-(4-methyl-1-piperazinyl)propoxy]-3-quinolinecarbonitrile (10 g) and 200 mL of methanol were heated to 65° C. and held with stirring for 30 minutes. The hot mixture was cooled to room temperature and filtered. The material obtained was washed with 80 mL MeOH and dried in vacuo to give 8.31 g of 4-[(2,4-dichloro-5-methoxyphenyl)amino]-6-methoxy-7-[3-(4-methyl-1-piperazinyl)propoxy]-3-quinolinecarbonitrile methanolate Form VI by XRD scans.

EXAMPLE 8

Preparation of 4-[(2,4-dichloro-5-methoxyphenyl) amino]-6-methoxy-7-[3-(4-methyl-1-piperazinyl) propoxy]-3-quinolinecarbonitrile monohydrate, Form I, from Form II 4-[(2,4-Dichloro-5-methoxyphenyl)amino]-6-methoxy-7-[3-(4-methyl-1-piperazinyl)propoxy]-3-quinolinecarbonitrile, Form II (1.0 g) was refluxed for 16 hours with 30 ml of water. The mixture was cooled to room temperature and filtered. The cake was washed with 10 ml of water and vacuum dried at 45° C. to give 0.89 g of 4-[(2,4-dichloro-5-methoxyphenyl)amino]-6-methoxy-7-[3-(4-methyl-1-piperazinyl) propoxy]-3-quinolinecarbonitrile monohydrate, Form I by XRD scans.

EXAMPLE 9

Preparation of 4-[(2,4-dichloro-5-methoxyphenyl) amino]-6-methoxy-7-[3-(4-methyl-1-piperazinyl) propoxy]-3-quinolinecarbonitrile monohydrate, Form I, from Form III 4-[(2,4-Dichloro-5-methoxyphenyl)amino]-6-methoxy-7-[3-(4-methyl-1-piperazinyl)propoxy]-3-quinolinecarbonitrile, Form III (2.0 g) was stirred for 24 hours with 40 ml of water at 95° C. The mixture was cooled to room temperature and filtered. The cake was washed with 10 ml of water and vacuum dried at 45° C. to give 1.83g of 4-[(2,4-dichloro-5-methoxyphenyl)amino]-6-methoxy-7-[3-(4-methyl-1-piperazinyl)propoxy]-3-quinolinecarbonitrile monohydrate, Form I by XRD scans.

EXAMPLE 10

Preparation of 4-[(2,4-dichloro-5-methoxyphenyl) amino]-6-methoxy-7-[3-(4-methyl-1-piperazinyl) propoxy]-3-quinolinecarbonitrile monohydrate, Form I, from Form III The wet 4-[(2,4-dichloro-5-methoxyphenyl)amino]-6-methoxy-7-[3-(4-methyl-1-piperazinyl)propoxy]-3-quinolinecarbonitrile monoisopropyl alcoholate, form III (6.28 g) from example 5, and 40 mL of water were added to a 100-mL flask.

The mixture was heated to 95° C. and sampled after 3, 5, and 20 hours. All three samples gave of 4-[(2,4-dichloro-5- methoxyphenyl)amino]-6-methoxy-7-[3-(4-methyl-1-piperazinyl)propoxy]-3-quinolinecarbonitrile monohydrate, Form I by XRD scans.

EXAMPLE 11

Preparation of 4-[(2,4-dichloro-5-methoxyphenyl)amino]-6-methoxy-7-[3-(4-methyl-1-piperazinyl)propoxy]-3-quinolinecarbonitrile monohydrate, Form I, from form IV 4-[(2,4-dichloro-5-methoxyphenyl)amino]-6-methoxy-7-[3-(4-methyl-1-piperazinyl)propoxy]-3-quinolinecarbonitrile, Form IV (1.0 g) was refluxed for 24 hours with 20 ml of water. The mixture was cooled to 35° C. and filtered. The cake was washed with 10 ml of water and vacuum dried at 45° C. to give 0.95 g of of 4-[(2,4-dichloro-5-methoxyphenyl)amino]-6-methoxy-7-[3-(4-methyl-1-piperazinyl)propoxy]-3-quinolinecarbonitrile monohydrate, Form I by XRD scans.

EXAMPLE 12

Preparation of 4-[(2,4-dichloro-5-methoxyphenyl)amino]-6-methoxy-7-[3-(4-methyl-1-piperazinyl)propoxy]-3-quinolinecarbonitrile monohydrate, Form I, from form VI 4-[(2,4-dichloro-5-methoxyphenyl)amino]-6-methoxy-7-[3-(4-methyl-1-piperazinyl)propoxy]-3-quinolinecarbonitrile methanolate, Form VI (1.0 g) was heated with stirring for 5 hours at 95° C. in 12 mL of water. The mixture was cooled to room temperature and filtered. The cake was washed with 2 mL water and vacuum dried at 45° C. to give 0.9 g of of 4-[(2,4-dichloro-5-methoxyphenyl)amino]-6-methoxy-7-[3-(4-methyl-1-piperazinyl)propoxy]-3-quinolinecarbonitrile monohydrate, Form I by XRD scans.

What is claimed is:

1. An isolated crystalline form of 4-[(2,4-dichloro-5-methoxyphenyl)amino]-6-methoxy-7-[3-(4-methyl-1-piperazinyl)propoxy]-3-quinolinecarbonitrile monohydrate having an x-ray diffraction pattern wherein at least one of the 2θ angles (°) of the significant peaks are at about: 9.19, 11.48, 14.32, 19.16, 19.45, 20.46, 21.29, 22.33, 23.96, 24.95, 25.29, 25.84, 26.55, 27.61, and 29.51.

2. The crystalline form of 4-[(2,4-dichloro-5-methoxyphenyl)amino]-6-methoxy-7-[3-(4-methyl-1-piperazinyl)propoxy]-3-quinolinecarbonitrile monohydrate of claim 1, having an x-ray diffraction pattern wherein 2θ angles (°) of significant peaks are at about: 9.19, 9.98, 11.48, 14.32, 14.85, 15.64, 19.16, 19.45, 19.71, 20.46, 21.29, 22.33, 22.58, 23.96, 24.95, 25.29, 25.84, 26.55, 27.61, 28.42, 29.51, 30.32, 31.40, and 32.39.

3. The crystalline form of 4-[(2,4-dichloro-5-methoxyphenyl)amino]-6-methoxy-7-[3-(4-methyl-1-piperazinyl)propoxy]-3-quinolinecarbonitrile monohydrate of claim 2, having the x-ray diffraction pattern substantially as shown in FIG. 1 as Pattern A.

4. An isolated crystalline form of 4-[(2,4-dichloro-5-methoxyphenyl)amino]-6-methoxy-7-[3-(4-methyl-1-piperazinyl)propoxy]-3-quinolinecarbonitrile monohydrate having a transition temperature to a liquid of about 109° C. to about 115° C.

5. The crystalline form of 4-[(2,4-dichloro-5-methoxyphenyl)amino]-6-methoxy-7-[3-(4-methyl-1-piperazinyl)propoxy]-3-quinolinecarbonitrile monohydrate of claim 4, wherein the transition temperature to a liquid is about 112° C.

6. A method of preparing 4-[(2,4-dichloro-5-methoxyphenyl)amino]-6-methoxy-7-[3-(4-methyl-1-piperazinyl)propoxy]-3-quinolinecarbonitrile monohydrate (Form I) comprising the step of treating anhydrous 4-[(2,4-dichloro-5-methoxyphenyl)amino]-6-methoxy-7-[3-(4-methyl-1-piperazinyl)propoxy]-3-quinolinecarbonitrile with heated water.

7. A method of preparing 4-[(2,4-dichloro-5-methoxyphenyl)amino]-6-methoxy-7-[3-(4-methyl-1-piperazinyl)propoxy]-3-quinolinecarbonitrile monohydrate (Form I) comprising the step of converting polymorphs of 4-[(2,4-dichloro-5-methoxyphenyl)amino]-6-methoxy-7-[3-(4-methyl-1-piperazinyl)propoxy]-3-quinolinecarbonitrile, which have a x-ray diffraction pattern substantially the same as one of Patterns B, C, and D, as shown in FIG. 1 and as Form VI pattern in FIG. 11, by treatment with water.

8. The method of claim 6, wherein the water is heated to at least about 90° C.

9. The method of claim 8, wherein the water is heated to at least about 95° C.

10. The method of claim 7, wherein the water is at a temperature where no heat source or cold source is applied.

11. The method of claim 10, wherein the water is at room temperature.

12. A pharmaceutical composition comprising a therapeutically effective amount of crystalline 4-[(2,4-dichloro-5-methoxyphenyl)amino]-6-methoxy-7-[3-(4-methyl-1-piperazinyl)propoxy]-3-quinolinecarbonitrile and a pharmaceutically acceptable carrier, wherein more than 50% by weight of said therapeutically effective amount consists of a crystalline form having an x-ray diffraction pattern substantially as shown in FIG. 1 as Pattern A and in FIG. 11 as Form I.

13. The composition of claim 12, further comprising acetic acid.

14. The composition of claim 12, further comprising a detergent.

15. The composition of claim 12, further comprising about 0.5% to about 5.0% by weight of a detergent and about 0.01% to about 0.1% by weight acetic acid.

16. The composition of claim 12, further comprising about 2.0% by weight detergent and about 0.06% by weight acetic acid.

17. The composition of claim 12, wherein the pharmaceutically acceptable carrier is selected from a sugar, a polyol and cellulose, or a combination thereof.

18. The composition of claim 17, wherein the pharmaceutically acceptable carrier is a polyol and cellulose.

19. The composition of claim 18, wherein the polyol is selected from mannitol, sorbitol and xylitol.

20. The composition of claim 19, wherein the polyol is mannitol.

21. The composition of claim 20, wherein the crystalline form of 4-[(2,4-dichloro-5-methoxyphenyl)amino]-6-methoxy-7-[3-(4-methyl-1-piperazinyl)propoxy]-3-quinolinecarbonitrile, the mannitol and the cellulose are individually present in amounts of about 20 to about 50 percent by weight.

* * * * *